United States Patent
Hammer

(10) Patent No.: US 9,510,866 B2
(45) Date of Patent: Dec. 6, 2016

(54) PIVOTING SPINAL FIXATION DEVICES

(75) Inventor: Michael Hammer, Pine Brook, NJ (US)

(73) Assignee: BLACKSTONE MEDICAL, INC., Lewisville, TX (US)

( * ) Notice: Subject to any disclaimer, the term of this patent is extended or adjusted under 35 U.S.C. 154(b) by 309 days.

(21) Appl. No.: 13/586,727

(22) Filed: Aug. 15, 2012

(65) Prior Publication Data

US 2014/0052189 A1    Feb. 20, 2014

(51) Int. Cl.
*A61B 17/70*    (2006.01)

(52) U.S. Cl.
CPC ....... *A61B 17/7032* (2013.01); *A61B 17/7007* (2013.01); *A61B 17/7049* (2013.01); *A61B 17/7055* (2013.01); *A61B 2090/037* (2016.02)

(58) Field of Classification Search
CPC .......... A61B 17/7001; A61B 17/7041; A61B 17/7043; A61B 17/7049; A61B 17/7037; A61B 17/7055; A61B 17/7032; A61B 17/7007
USPC ........... 606/60, 246–279, 300–320, 325–328
See application file for complete search history.

(56) References Cited

U.S. PATENT DOCUMENTS

| | | | |
|---|---|---|---|
| 5,261,907 A | 11/1993 | Vignaud et al. | |
| 5,312,405 A * | 5/1994 | Korotko | A61B 17/7052 606/252 |
| 5,527,314 A | 6/1996 | Brumfield et al. | |
| 5,545,167 A * | 8/1996 | Lin | A61B 17/7037 411/349 |
| 5,676,665 A | 10/1997 | Bryan | |
| 5,713,898 A * | 2/1998 | Stucker | A61B 17/7044 606/280 |
| 5,899,905 A * | 5/1999 | Errico | A61B 17/7032 606/256 |
| 5,928,233 A * | 7/1999 | Apfelbaum | A61B 17/7055 606/261 |
| 5,964,760 A * | 10/1999 | Richelsoph | A61B 17/7037 606/278 |
| 5,980,521 A * | 11/1999 | Montague | A61B 17/7052 606/250 |
| 5,989,250 A * | 11/1999 | Wagner | A61B 17/7038 606/250 |
| 6,171,311 B1 * | 1/2001 | Richelsoph | A61B 17/7049 606/250 |
| 6,238,396 B1 * | 5/2001 | Lombardo | A61B 17/7052 606/251 |

(Continued)

FOREIGN PATENT DOCUMENTS

| | | |
|---|---|---|
| EP | 1665994 A1 | 7/2006 |
| EP | 1762195 A1 | 3/2007 |

OTHER PUBLICATIONS thefreedictionary.com definition of "rod". thefreedictionary.com/rod. Accessed on Feb. 4, 2015.*

(Continued)

*Primary Examiner* — Lynnsy Summitt
(74) *Attorney, Agent, or Firm* — Baker & McKenzie LLP

(57) ABSTRACT

Disclosed embodiments relate to connector systems comprising a linking element, a rod connection element partially received in the linking element. In an embodiment, the rod connection element is operable to rotate about the first longitudinal axis relative to the linking element. A fastener is operable to be received in the rod connection element, wherein the fastener is operable to actuate a connection mechanism to substantially fix the rod connection element in a rotational orientation relative to the first longitudinal axis and substantially fix the rod in a longitudinal position relative to the rod connection element.

20 Claims, 9 Drawing Sheets

(56) References Cited

U.S. PATENT DOCUMENTS

| | | | |
|---|---|---|---|
| 6,328,740 B1* | 12/2001 | Richelsoph | A61B 17/7049 606/252 |
| 6,352,537 B1 | 3/2002 | Strnad | |
| 6,524,315 B1* | 2/2003 | Selvitelli | A61B 17/7044 606/278 |
| 6,547,790 B2* | 4/2003 | Harkey, III | A61B 17/7044 606/250 |
| 6,572,622 B1* | 6/2003 | Schafer | A61B 17/7044 606/272 |
| 6,592,585 B2* | 7/2003 | Lee | A61B 17/7002 606/252 |
| 6,595,992 B1* | 7/2003 | Wagner | A61B 17/7034 606/250 |
| 6,746,449 B2* | 6/2004 | Jones | A61B 17/7037 606/279 |
| 6,776,781 B1* | 8/2004 | Uwaydah | A61B 17/7059 606/279 |
| 6,866,664 B2* | 3/2005 | Schär | A61B 17/7052 606/246 |
| 6,869,432 B2* | 3/2005 | Schlapfer | A61B 17/60 606/280 |
| 6,945,972 B2* | 9/2005 | Frigg | A61B 17/7041 606/256 |
| 7,087,057 B2* | 8/2006 | Konieczynski | A61B 17/7032 606/278 |
| 7,186,255 B2* | 3/2007 | Baynham | A61B 17/7035 606/266 |
| 7,189,236 B2* | 3/2007 | Taylor | A61B 17/7055 606/277 |
| 7,232,441 B2* | 6/2007 | Altarac | A61B 17/7055 606/250 |
| 7,303,563 B2* | 12/2007 | Poyner | A61B 17/8061 606/250 |
| 7,524,323 B2* | 4/2009 | Malandain | A61B 17/7007 606/246 |
| 7,585,312 B2* | 9/2009 | Rawlins | A61B 17/7041 606/246 |
| 7,585,314 B2* | 9/2009 | Taylor | A61B 17/705 606/250 |
| 7,618,418 B2* | 11/2009 | Malandain | A61B 17/7007 606/60 |
| 7,618,443 B2* | 11/2009 | Abdou | A61B 17/6433 606/267 |
| 7,621,942 B2* | 11/2009 | Piehl | A61B 17/8061 606/279 |
| 7,645,294 B2 | 1/2010 | Kalfas et al. | |
| 7,651,496 B2* | 1/2010 | Keegan | A61B 17/0293 128/898 |
| 7,678,136 B2* | 3/2010 | Doubler | A61B 17/7007 606/246 |
| 7,776,070 B2* | 8/2010 | Null | A61B 17/7055 606/252 |
| 7,799,059 B2* | 9/2010 | Kramer | A61B 17/7035 606/256 |
| 7,976,567 B2* | 7/2011 | Null | A61B 17/7041 606/250 |
| 8,002,803 B2* | 8/2011 | Winslow | A61B 17/7035 606/246 |
| 8,012,188 B2* | 9/2011 | Melkent | A61B 17/7007 606/286 |
| 8,034,086 B2* | 10/2011 | Iott | A61B 17/7032 606/267 |
| 8,080,037 B2* | 12/2011 | Butler | A61B 17/7052 606/250 |
| 8,083,776 B2* | 12/2011 | Alvarez | A61B 17/7032 606/265 |
| 8,109,976 B2* | 2/2012 | Lim | A61B 17/7001 606/250 |
| 8,118,837 B2* | 2/2012 | Lemoine | A61B 17/7049 606/246 |
| 8,177,823 B2* | 5/2012 | Lake | A61B 17/7044 606/276 |
| 8,197,515 B2* | 6/2012 | Levy | A61B 17/7052 606/250 |
| 8,241,334 B2* | 8/2012 | Butler | A61B 17/7052 606/251 |
| 8,246,662 B2* | 8/2012 | Lemoine | A61B 17/7055 606/250 |
| 8,262,700 B2* | 9/2012 | Cho | A61B 17/7049 606/250 |
| 8,262,702 B2* | 9/2012 | Giger | A61B 17/7035 606/246 |
| 8,277,489 B2* | 10/2012 | Saidha | A61B 17/7049 606/250 |
| 8,298,269 B2* | 10/2012 | Null | A61B 17/705 606/250 |
| 8,317,833 B2* | 11/2012 | Lange | A61B 17/7031 606/256 |
| 8,388,659 B1* | 3/2013 | Lab | A61B 17/7037 606/265 |
| 8,394,131 B2* | 3/2013 | Wing | 606/264 |
| 8,414,616 B2* | 4/2013 | Berrevoets | A61B 17/7044 606/250 |
| 8,414,623 B2* | 4/2013 | Baker | A61B 17/705 606/264 |
| 8,430,913 B2* | 4/2013 | James | A61B 17/7005 606/264 |
| 8,506,567 B2* | 8/2013 | Ziemek | A61B 17/8042 606/296 |
| 8,523,906 B2* | 9/2013 | McLean | A61B 17/7011 606/246 |
| 8,556,942 B2* | 10/2013 | Ziolo | A61B 17/7055 606/280 |
| 8,585,741 B2* | 11/2013 | Gabelberger | A61B 17/7035 606/264 |
| 8,591,550 B2* | 11/2013 | Ludwig | A61B 17/7007 606/246 |
| 8,636,737 B2* | 1/2014 | Lemoine | A61B 17/7055 606/252 |
| 8,641,719 B2* | 2/2014 | Gephart | A61B 17/3421 606/279 |
| 8,663,281 B2* | 3/2014 | McLean | A61B 17/7011 606/246 |
| 8,668,720 B2* | 3/2014 | Perez-Cruet | A61B 17/7005 606/255 |
| 8,668,721 B2* | 3/2014 | Miller | A61B 17/7041 606/264 |
| 8,672,978 B2* | 3/2014 | Dant | A61B 17/7032 606/250 |
| 8,672,983 B2* | 3/2014 | Biscup | A61B 17/7007 606/267 |
| 8,690,923 B2* | 4/2014 | Lynch | A61B 17/705 606/246 |
| 8,709,049 B2* | 4/2014 | Klein | A61B 17/7007 606/259 |
| 8,715,323 B2* | 5/2014 | Ballard | A61B 17/7049 606/278 |
| 8,740,953 B2* | 6/2014 | Hoffman | A61B 17/7055 606/257 |
| 8,758,411 B1* | 6/2014 | Rayon | A61B 17/7004 606/259 |
| 2004/0172022 A1* | 9/2004 | Landry | A61B 17/1604 606/86 A |
| 2005/0124994 A1* | 6/2005 | Berger | A61B 17/7055 606/256 |
| 2005/0137596 A1* | 6/2005 | Uwaydah | A61B 17/7059 606/281 |
| 2005/0240181 A1* | 10/2005 | Boomer | A61B 17/7041 606/914 |
| 2005/0251141 A1* | 11/2005 | Frigg | A61B 17/7041 606/301 |
| 2006/0036252 A1 | 2/2006 | Baynham et al. | |
| 2006/0058794 A1* | 3/2006 | Jackson | A61B 17/7032 606/272 |
| 2006/0069389 A1* | 3/2006 | Knopfle | A61C 8/0031 433/24 |
| 2006/0079892 A1* | 4/2006 | Roychowdhury | A61B 17/7044 606/253 |
| 2006/0149252 A1* | 7/2006 | Markworth | A61B 17/7005 606/900 |
| 2006/0241596 A1* | 10/2006 | Rezach | A61B 17/7041 606/264 |
| 2006/0247626 A1 | 11/2006 | Taylor et al. | |

(56) References Cited

U.S. PATENT DOCUMENTS

| | | | |
|---|---|---|---|
| 2007/0118121 A1* | 5/2007 | Purcell | A61B 17/7055 606/261 |
| 2007/0123869 A1* | 5/2007 | Chin | A61B 17/7044 606/276 |
| 2007/0293861 A1* | 12/2007 | Rezach | A61B 17/7037 606/60 |
| 2007/0299441 A1* | 12/2007 | Hoffman | A61B 17/7055 606/250 |
| 2008/0114400 A1* | 5/2008 | Dant | A61B 17/7049 606/246 |
| 2008/0132957 A1* | 6/2008 | Matthis | A61B 17/7032 606/301 |
| 2008/0140124 A1* | 6/2008 | Jeon | A61B 17/7049 606/278 |
| 2008/0147123 A1* | 6/2008 | Schermerhorn | A61B 17/7011 606/278 |
| 2008/0177327 A1* | 7/2008 | Malandain | A61B 17/7011 606/278 |
| 2009/0036929 A1 | 2/2009 | Reglos et al. | |
| 2009/0125067 A1* | 5/2009 | Mazzuca | A61B 17/7055 606/280 |
| 2010/0036432 A1* | 2/2010 | Ely | A61B 17/7032 606/301 |
| 2010/0087864 A1* | 4/2010 | Klein | A61B 17/7007 606/264 |
| 2010/0087867 A1* | 4/2010 | Klein | A61B 17/7007 606/278 |
| 2010/0094346 A1* | 4/2010 | Matityahu | A61B 17/7038 606/250 |
| 2010/0094349 A1* | 4/2010 | Hammer | A61B 17/7034 606/264 |
| 2010/0121384 A1* | 5/2010 | Abdou | A61B 17/6433 606/301 |
| 2010/0318131 A1 | 12/2010 | James et al. | |
| 2011/0040335 A1* | 2/2011 | Stihl | A61B 17/7032 606/302 |
| 2011/0106164 A1* | 5/2011 | Wilcox | A61B 17/7037 606/264 |
| 2011/0106166 A1* | 5/2011 | Keyer | A61B 17/705 606/264 |
| 2011/0190824 A1* | 8/2011 | Gephart | A61B 17/70 606/278 |
| 2011/0251643 A1* | 10/2011 | Miladi | A61B 17/7001 606/254 |
| 2011/0270316 A1* | 11/2011 | Piehl | A61B 17/8061 606/264 |
| 2011/0270325 A1* | 11/2011 | Keyer | A61B 17/7037 606/305 |
| 2011/0307018 A1* | 12/2011 | Zucherman | A61B 17/7007 606/266 |
| 2012/0010661 A1* | 1/2012 | Farris | A61B 17/7037 606/264 |
| 2012/0065686 A1* | 3/2012 | Black | A61B 17/7055 606/252 |
| 2012/0071926 A1* | 3/2012 | Jani | A61B 17/7049 606/250 |
| 2012/0109206 A1* | 5/2012 | Abdou | A61B 17/6433 606/250 |
| 2012/0130436 A1* | 5/2012 | Haskins | A61B 17/7032 606/305 |
| 2012/0232593 A1* | 9/2012 | Predick | A61B 17/7049 606/250 |
| 2012/0303062 A1* | 11/2012 | Amstutz | A61B 17/7041 606/267 |
| 2013/0006306 A1* | 1/2013 | Saidha | A61B 17/7049 606/252 |
| 2013/0006307 A1* | 1/2013 | Robinson | A61B 17/7052 606/252 |
| 2013/0053889 A1* | 2/2013 | Lange | A61B 17/7031 606/259 |
| 2013/0085534 A1* | 4/2013 | Hainard | A61B 17/7055 606/278 |
| 2013/0172938 A1* | 7/2013 | Ziolo | A61B 17/7055 606/279 |
| 2013/0184760 A1* | 7/2013 | Ballard | A61B 17/7041 606/278 |
| 2013/0253588 A1* | 9/2013 | Traynelis | A61B 17/7005 606/269 |
| 2014/0005726 A1* | 1/2014 | Jackson | A61B 17/7032 606/273 |
| 2014/0012323 A1* | 1/2014 | de Coninck | A61B 17/7059 606/279 |
| 2014/0046375 A1* | 2/2014 | Ziolo | A61B 17/7055 606/279 |
| 2014/0052181 A1* | 2/2014 | Lemoine | A61B 17/7055 606/246 |
| 2014/0088651 A1* | 3/2014 | Ludwig | A61B 17/7007 606/268 |

OTHER PUBLICATIONS

International Search Report and Written Opinion, PCT/US2013/052371, dated Jan. 9, 2014, 9 pages.

Extended European Search Report, EP Application No. 13829995.3 (PCT/US2013/052371); dated Mar. 10, 2016, 13 pages.

* cited by examiner

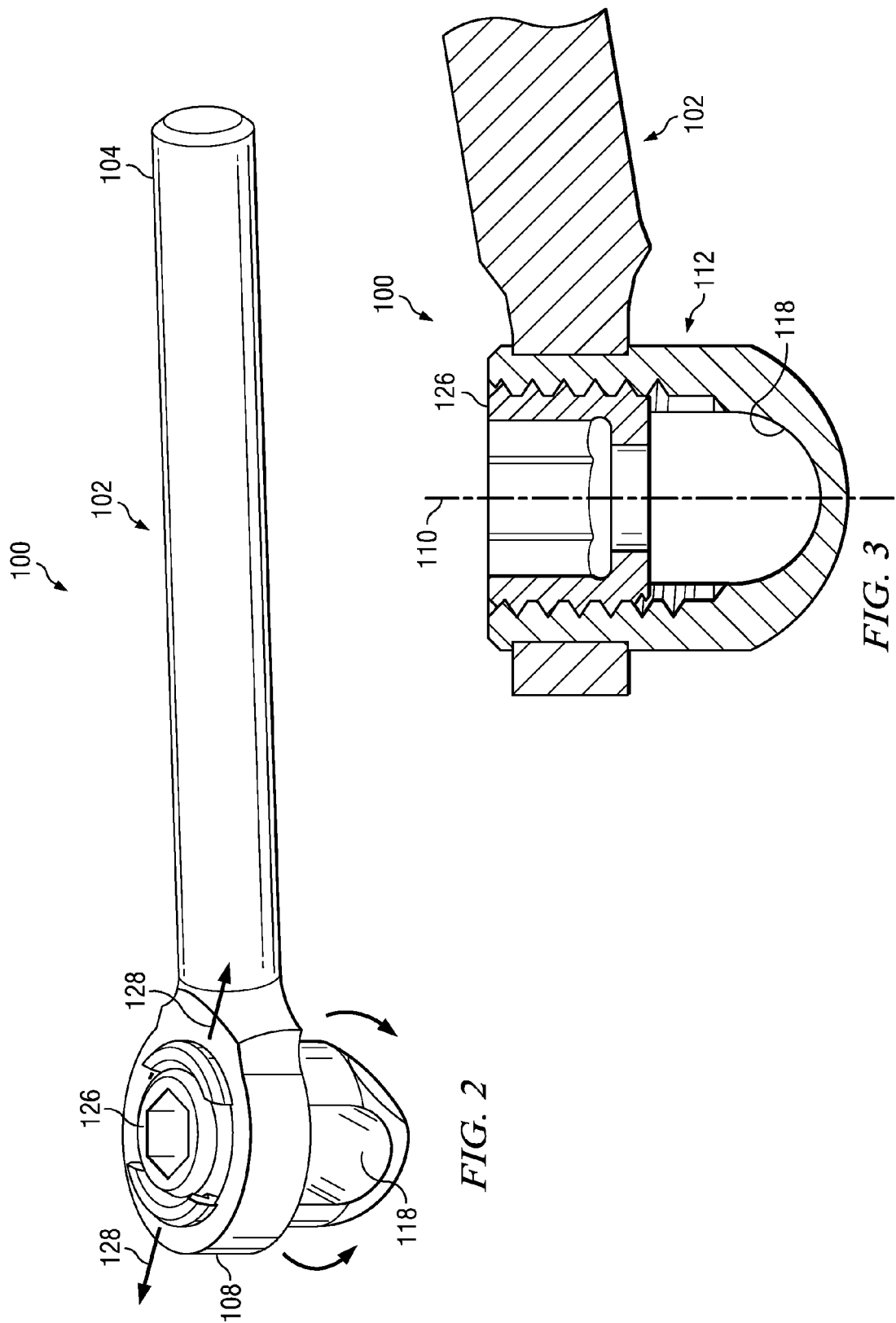

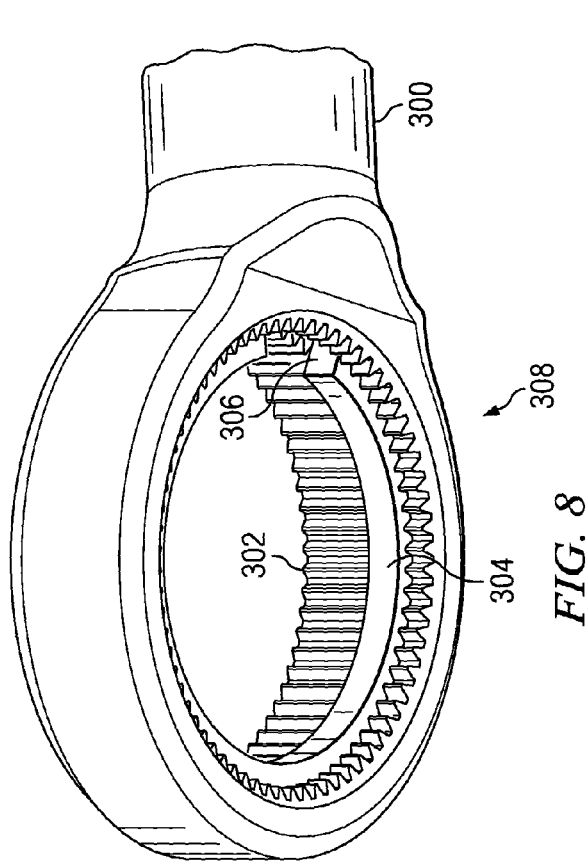
FIG. 8
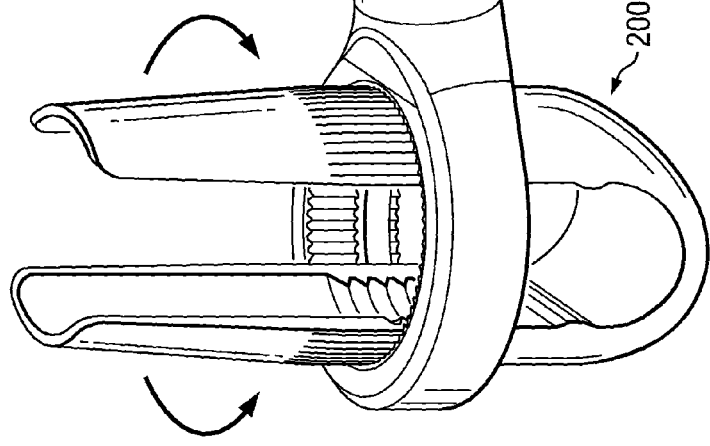
FIG. 9

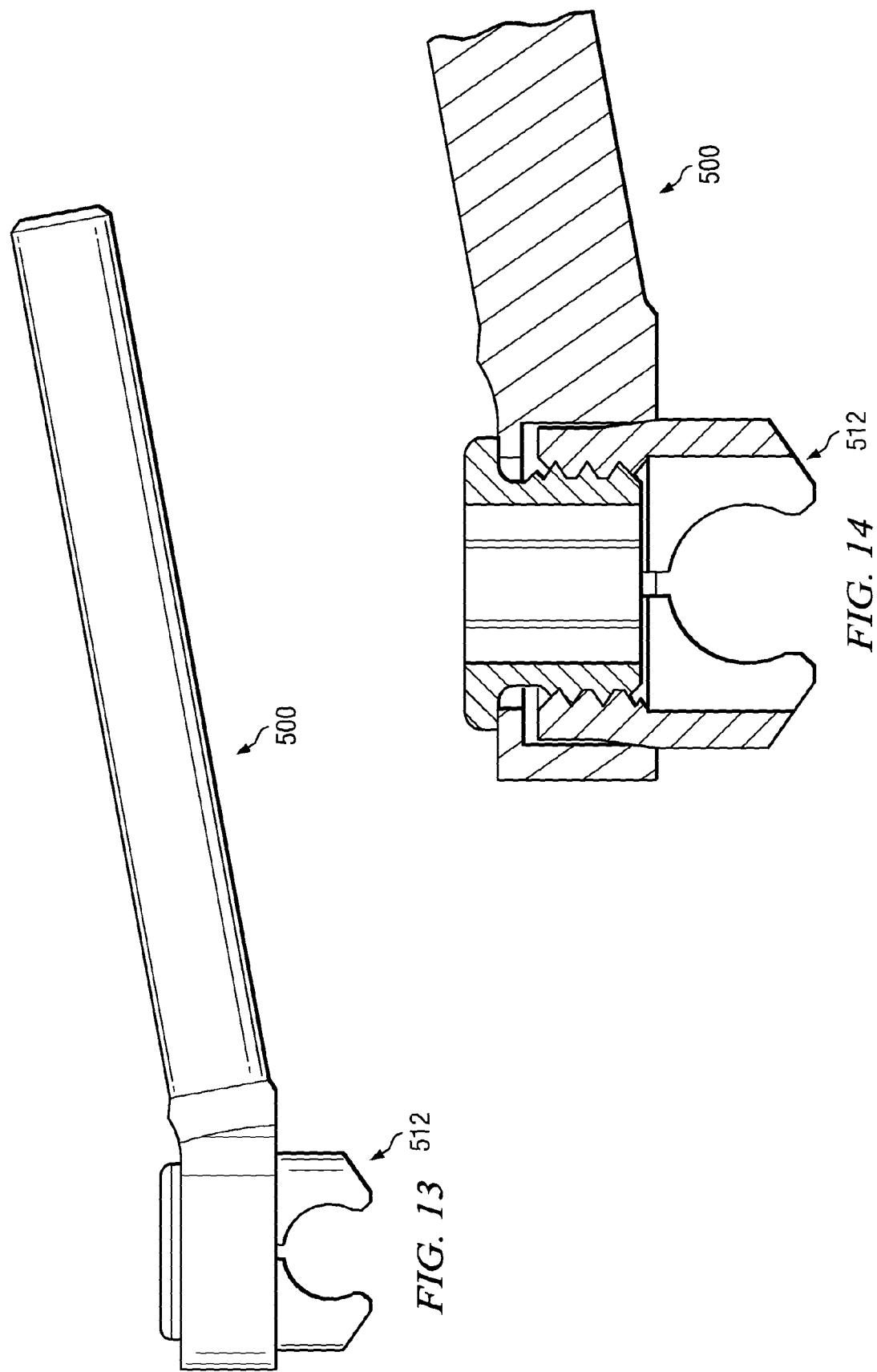

PIVOTING SPINAL FIXATION DEVICES

TECHNICAL FIELD

The disclosed embodiments relate generally to orthopedic devices, and more specifically to spinal fixation devices.

BACKGROUND

Spinal fixation devices may be used to stabilize or align a patient's spine. Exemplary spinal fixation devices include pedicle screw assemblies which may involve attaching spinal rods adjacent the vertebrae of interest with pedicle screws. Conventional pedicle screw assemblies may include pedicle screws that are disposed through the construct rod or pedicle screws that are disposed at an offset position from the construct rod.

SUMMARY

In accordance with the present disclosure, an embodiment of an orthopedic connector system comprising a linking element having an end portion operable to be connected to a fastening device, and an aperture defined in an offset portion of the linking element offset from the end portion, the aperture extending along a first longitudinal axis. The connector system also includes a rod connection element having an upper portion operable to be received in the aperture, wherein the rod connection element is operable to rotate about the first longitudinal axis relative to the linking element. The rod connection element may comprise an opening defined in the upper portion of the rod connection element, the opening extending longitudinally along and circumferentially about the first longitudinal axis, and an elongated slot defined in a lower portion of the rod connection element, the elongated slot operable to receive a rod therein. The connector system also includes a fastener operable to be received in the opening of the rod connection element. The fastener may be operable to actuate a connection mechanism to substantially fix the rod connection element in a rotational orientation relative to the first longitudinal axis and substantially fix the rod in a longitudinal position relative to the rod connection element.

In accordance with the present disclosure, an embodiment of an orthopedic connector system comprising a linking element having an end portion operable to be connected to a fastening device, and an aperture defined in an offset portion of the linking element offset from the end portion, the aperture extending along a first longitudinal axis. The disclosed connector system further includes a rod connection element having an upper portion operable to be received in the aperture, wherein the rod connection element is operable to rotate about the first longitudinal axis relative to the linking element. The rod connection element comprises an opening defined in the upper portion of the rod connection element, the opening extending longitudinally along and circumferentially about the first longitudinal axis, and a tapered flexible lower portion operable to clamp onto a rod. The disclosed connector system further includes a fastener comprising a head portion operable to latch against a top surface of the offset portion and a body portion operable to be received in the opening of the rod connection element. In an embodiment, a rotation of the fastener is operable to effect a translation of the rod connection element upwardly towards the top surface of the offset portion and a compression of the tapered flexible lower portion of the rod connection element against an inner wall of the offset portion of the linking element, the compression operable to substantially fix the rod connection element in a rotational orientation relative to the first longitudinal axis and substantially fix the rod in a longitudinal position relative to the rod connection element.

Also disclosed herein is an exemplary method for assembling a connector system for connecting a medical fastener to a rod in an offset orientation. The disclosed method comprises connecting a rod connection element to a rod. The method further includes providing a linking element having an end portion operable to be connected to a fastening device and an aperture defined in an offset portion of the linking element offset from the end portion, the aperture extending along a first longitudinal axis. The method further includes disposing an upper portion of a rod connection element in the aperture, positioning the linking element in a rotational orientation about the first longitudinal axis relative to the rod connection element. The method further includes disposing a fastener in an opening defined in the upper portion of the rod connection element, the opening extending longitudinally along and circumferentially about the first longitudinal axis, and rotating the fastener to substantially fix the linking element relative to the rod connection element and substantially fix the rod in a longitudinal position relative to the rod connection element.

BRIEF DESCRIPTION OF THE DRAWINGS

For a more complete understanding of the present disclosure and its advantages, reference is now made to the following description taken in conjunction with the accompanying drawings, in which like reference numbers indicate like features, and:

FIG. 2 illustrates an assembled view of the connector system shown in FIG. 1;

FIG. 3 illustrates a partial cross-sectional view of the connector system shown in FIG. 2;

FIG. 8 illustrates a perspective view of an exemplary embodiment of a linking element;

FIG. 9 illustrates a perspective view of an exemplary linking element connected to an exemplary rod connection element;

FIG. 13 illustrates an assembled view of the connector system shown in FIG. 12; and FIG. 14 illustrates a partial cross-sectional view of the connector system shown in FIG. 13;

DETAILED DESCRIPTION

Offset style connector systems may be configured to be monolithic, which would not allow for rotational adjustment of the construct rod. Such a system may be difficult to assemble and attach to the patient, especially in certain anatomical space, such as that proximate to the sacrum and ilium.

Figure 1:
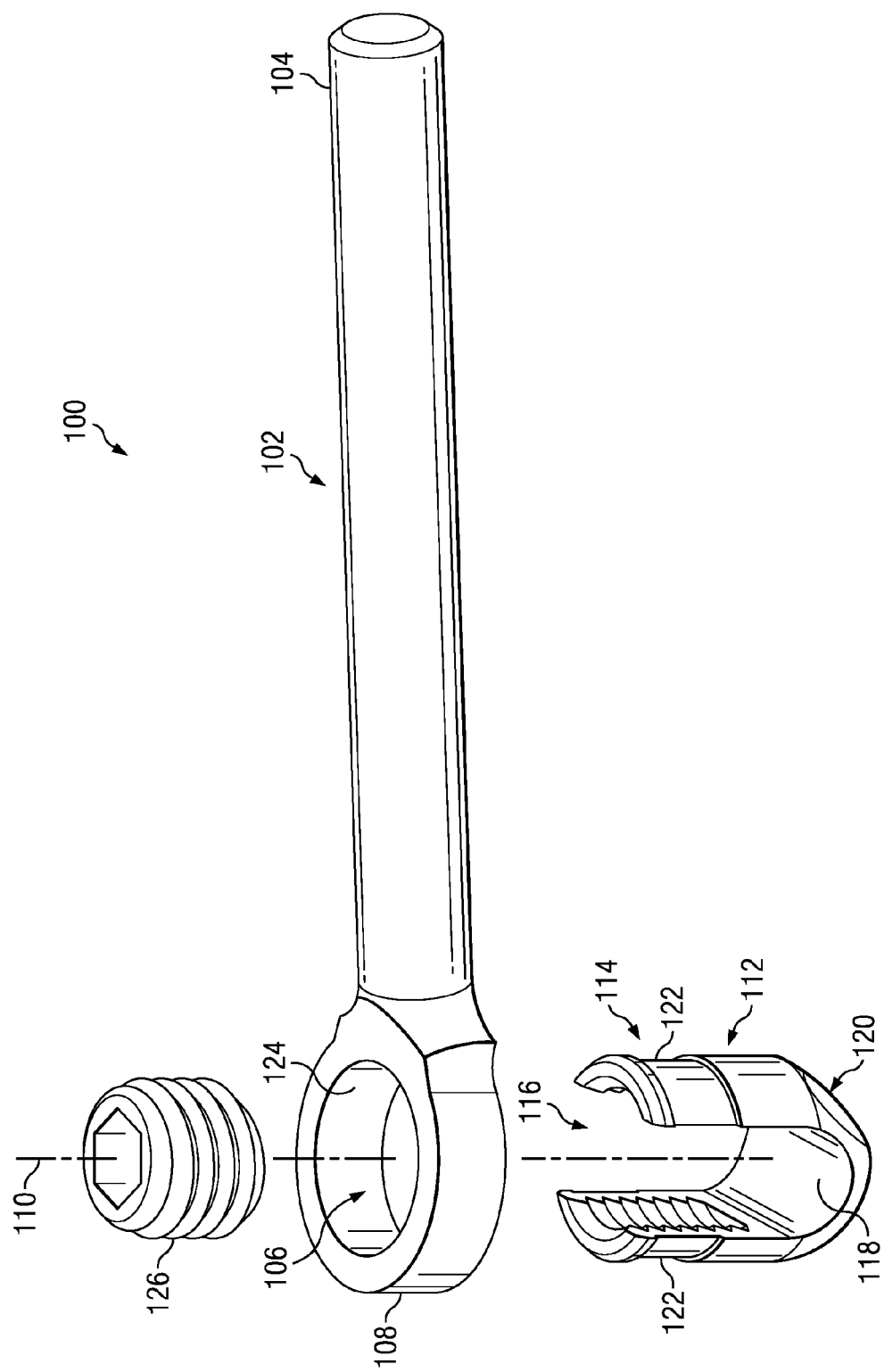
FIG. 1 illustrates an explode view of an exemplary embodiment of a connector system.

FIG. 1 and FIG. 2 illustrate an exemplary embodiment of an orthopedic connector system 100 before and after assembly, respectively. FIG. 3 is a cross-sectional view of the orthopedic connector system 100 in an assembled state. Referring to FIGS. 1-3, an exemplary embodiment of the orthopedic connector system 100 may include a linking element 102 having an end portion 104 operable to be connected to a fastening device (not shown), such a pedicle screw. The linking element 102 may also include an aperture 106 defined in an offset portion 108 of the linking element 102 offset from the end portion 104 The aperture 106 may extend along a first longitudinal axis 110. The end portion 104 of the linking element 102 may have a variety of configurations, including a rod-like geometry as shown in FIGS. 1-3. The aperture 106 may be offset from the end portion 104 by various distances and angles, depending on the surgical applications and the anatomical constraints in each application.

The orthopedic connector system 100 may also include a rod connection element 112 having an upper portion 114 operable to be received in the aperture 106. The upper portion 114 may include outer recessed areas 122 extending circumferentially that allow the rod connection element 112 to be snapped into the aperture 106 where the outer recessed areas 122 mate with the inner wall 124 of the offset portion 108 of the linking element 102. Configured as such, the linking element 102 is operable to rotate about the first longitudinal axis 110 relative to the rod connection element 112.

An embodiment of the rod connection element 112 includes an opening 116 defined in the upper portion 114 of the rod connection element 112, and the opening 116 may be configured to extend longitudinally along and circumferentially about the first longitudinal axis 110 as illustrated in FIGS. 1-3. An embodiment of the rod connection element 112 further includes an elongated slot 118 defined in a lower portion 120 of the rod connection element 112. The elongated slot 118 may be configured receive a rod (not shown), which may be any construct rod for connecting pedicle screws known in the art an will be described in greater details with respect to other exemplary embodiments disclosed herein.

The orthopedic connector system 100 may also include a fastener 126 operable to be received in the opening 116 of the rod connection element 112. The fastener 126 may be configured in a variety of ways to actuate a connection mechanism to substantially fix the rotational orientation of the linking element 102 about the first longitudinal axis 110 relative to the rod connection element 112 and substantially fix the rod in a longitudinal position relative to the rod connection element 112. In an exemplary embodiment, the fastener 126 may be a set screw as shown in FIGS. 1-3.

In operation, a construct rod (not shown) may be already implanted in a surgical site, and the rod connection element 112 may be connected to the construct rod such that the rod is received through the elongated slot 118. The upper portion 114 of the rod connection element 112 may be received in the aperture 106 of the linking element 102, and the end portion 104 of the linking element 102 may be passed through a pedicle screw's slot (not shown). A set screw (not shown) may then be inserted into the pedicle screw. The orientations of the linking element 102 relative to both the pedicle screw and rod connector element 112 may be adjusted, and the fastener 126 and the set screw of the pedicle screw may be provisionally tightened to ensure proper engagement between mating components is achieved. When the fastener 126 is tightened, a first compression force may be exerted by the fastener 126 on the upper portion 114 of the rod connection element 112 against an inner wall 124 of the offset portion 108 to substantially fix the rotational orientation of the linking element 102 about the first longitudinal axis 110 relative to the rod connection element 112. In an embodiment, the desired rotational orientation may be one that improves the ease of rod attachment to the rod connection element 112. Further, the tightening of the fastener 126 may allow for a second compression force exerted by the fastener 126 on the rod against the elongated slot 118 to substantially fix the rod in a longitudinal position relative to the elongated slot 118. As discussed above, the fastener 126 may be a set screw as illustrated in FIGS. 1-3. The illustrated set screw design comprises a standard unified screw thread, but, in an embodiment, a reverse buttress could also be employed to increase the force applied.

It is to be appreciated that the embodiments discussed with respect to FIGS. 1-3 allow an additional degree of adjustment when compared to mono-axial lateral offset designs and a reduction of the material under the rod. More specifically, the rotational connection between the rod connection element 112 and the offset portion 108 of the linking element 102 allows for an additional degree of rotational freedom while the fastener 126 allows for fixing the orientation of the rod connection element 112 and the orientation of the construct rod. As such, the construct rod and the linking element 102 do not need to be orthogonal to each other to enable attachment. This can be particularly helpful when pedicle screws are placed in both the sacrum and ilium. Offset connector attachment to construct rods can be hindered by the relative location of sacral and iliac screws and the rod orientation.

Figure 4:
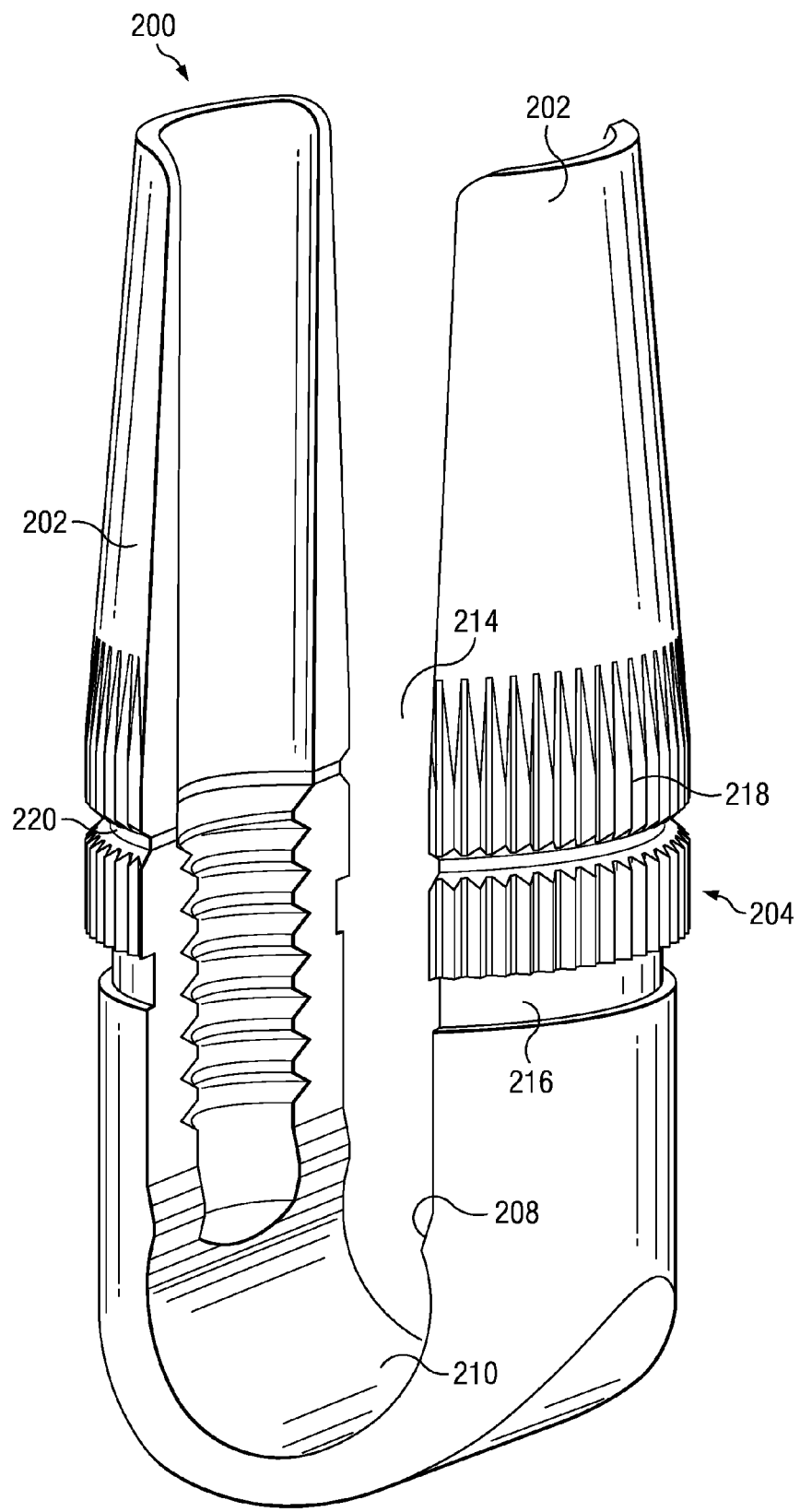
FIG. 4 illustrates a perspective view of an exemplary embodiment of a rod connection element.

It is to be appreciated that, in some applications, the ease of construct assembly of the embodiments of the present disclosure may be improved by modifying suitable aspects the connector system 100. By way of example, various exemplary embodiments in accordance with the present disclosure will be discussed with respect to FIGS. 4-11. FIG. 4 illustrates an exemplary rod connection element 200 that is different from the rod connection element 112 in a few aspects.

Figure 6:
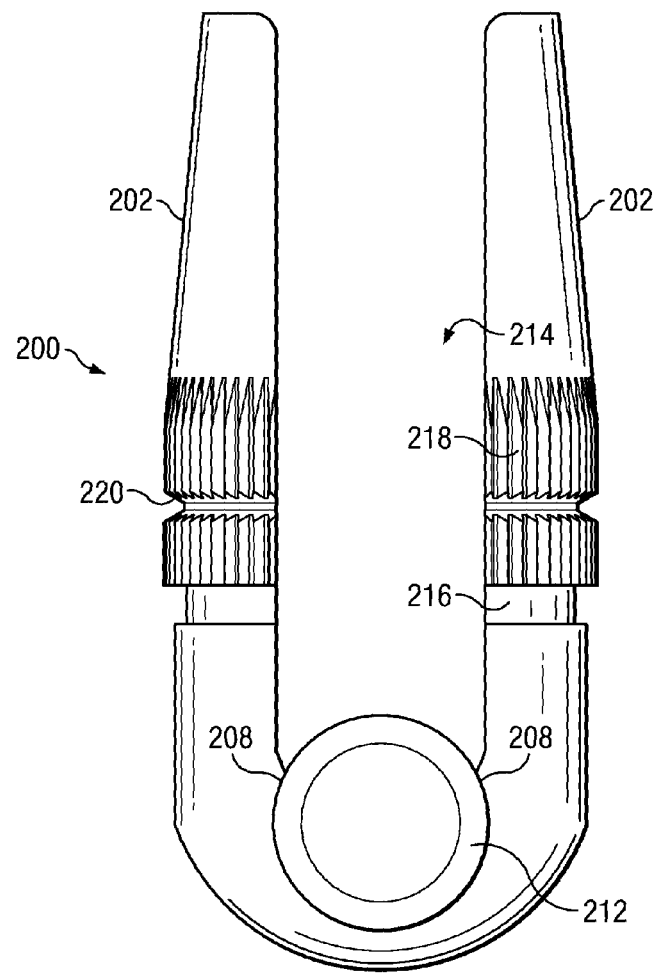
FIG. 6 illustrates a side view of the rod connection element shown in FIG. 4 with a rod.
Figure 7:
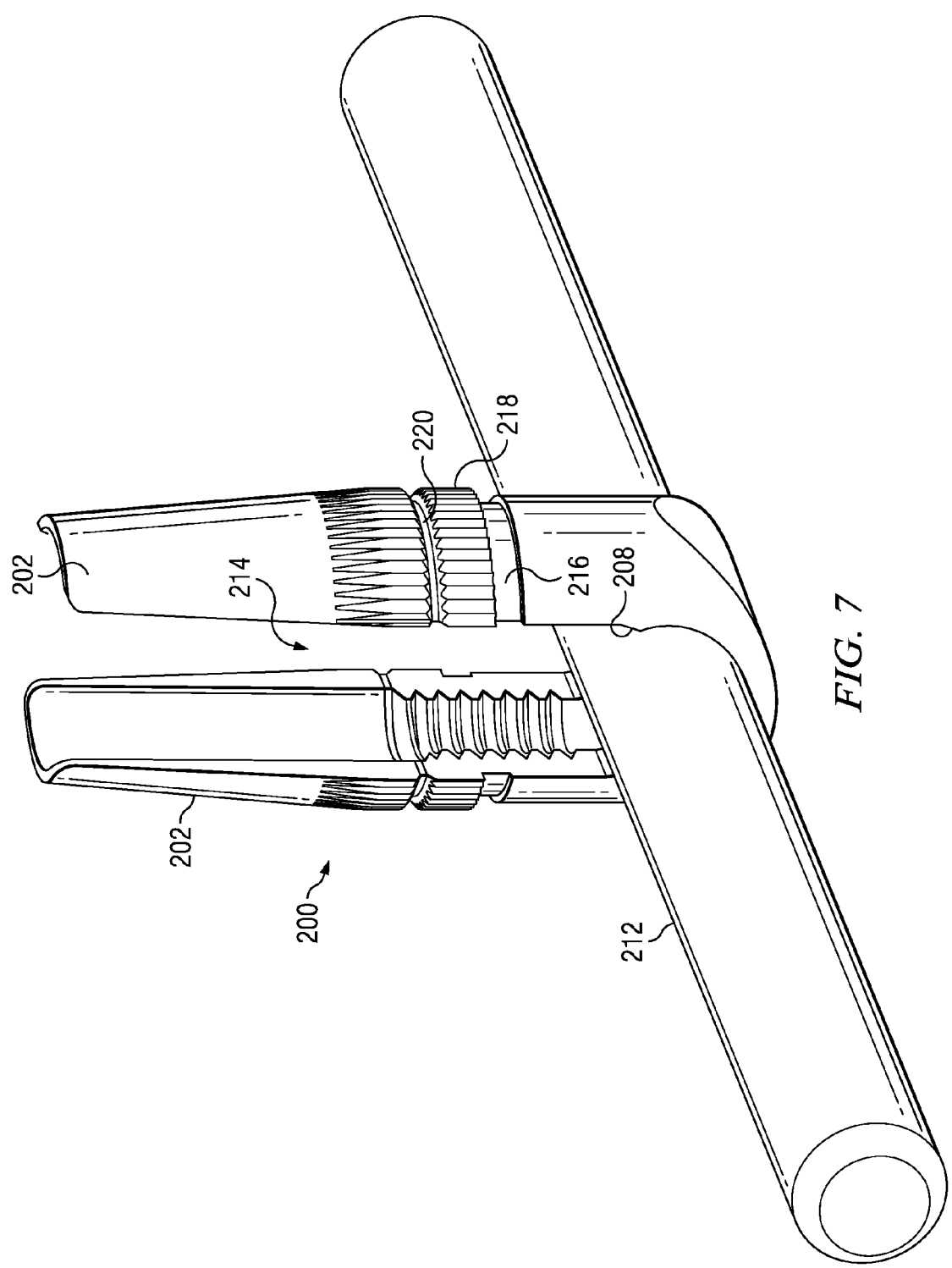
FIG. 7 illustrates a perspective view of an exemplary embodiment of the rod connection element shown in FIG. 4 receiving a rod.
Figure 10:
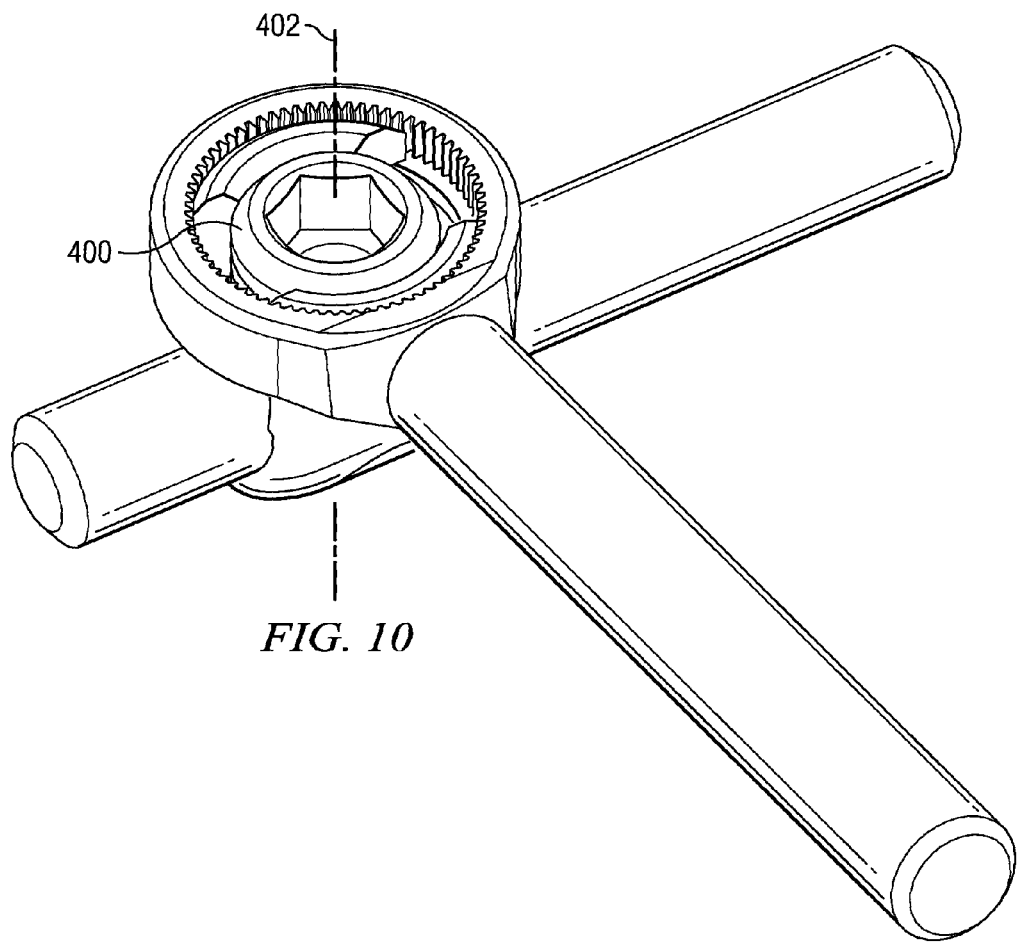
FIG. 10 illustrates a perspective view of an exemplary linking element rotationally fixed with respect to an exemplary rod connection element having a rod disposed therein.

In an embodiment, the rod 212 may be disposed into the slot 210 from the top side through the opening 214 defined in the upper portion 216 of the rod connection element 200 before the rod connection element 200 is assembled with the linking element 300. The slot 210 may have an undercut geometry that mates with the geometry of the rod 212 and a latch 208 proximate to the slot 210. The mating of the geometries and the latch 208 may allow a tight interference fit with the rod 212. To securely snap the rod 212 into the bottom of the slot 210 as shown in FIGS. 6 and 7, one may spread apart the rod connection element 200 to clear the latch 208, after which a clearance fit may minimize splay between the linking element 300, the rod connection element 200, and the fastener 126. It is to be appreciated that the top loading approach for snapping the rod 212 into the slot 210 may improve the ease of construct assembly in comparison to the more limited angle from the side when the top is closed (with the engagement of the linking element 300 onto the rod connection element 200). As such, a plurality of rod connection elements 200 may be snapped onto the rod 212 at various longitudinal positions as opposed to stringing a number of rod connection elements onto a contour rod.

In an embodiment, after the rod 212 is inserted, the linking element 300 may be disposed over the rod connection element 200 to close the top side. In an embodiment, the rod connection element 200 includes tabs 202 that taper diametrically as they extend upwardly from the upper portion 204 of the rod connection element 200. The tabs 202 are operable to guide the linking element 300 down to the upper portion 204 for engagement as shown in FIG. 9. The linking element 300 shown in FIG. 8 includes a plurality of longitudinal ridges 302 and a ring 304 disposed in a groove 306 defined in an inner wall of the offset portion 308. The groove 306 has a larger diameter than the ring 304 such that the ring 304 may expand into the groove 306 as the linking element 300 is placed over the rod connection element 200. As the linking element 300 advances, the ring 304 expands and then snaps into a mating groove 216 defined in the upper portion 204 of the rod connection element 200.

Figure 5:
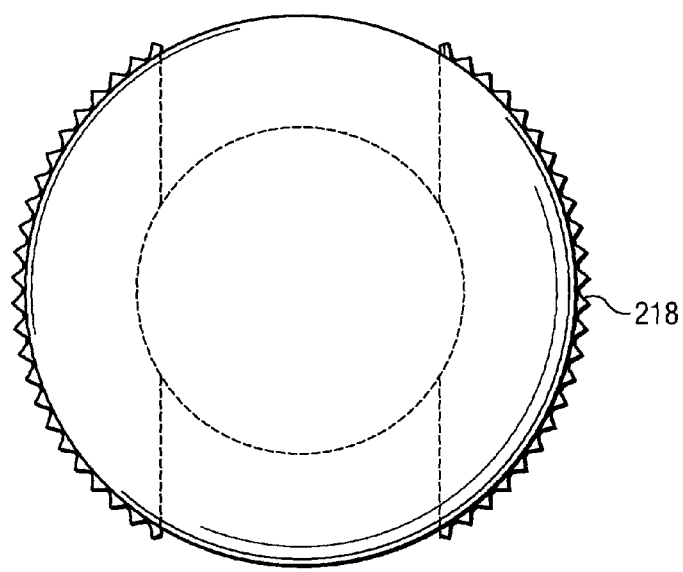
FIG. 5 illustrates a cross-sectional view of the rod connection element shown in FIG. 4.

The ridges 302 of the linking element 300 may mate with the ridges 218 defined in the upper portion 204 of the rod connection element 200. Referring to FIG. 5, which is a cross sectional view of the rod connection element 200, the pitch of the ridges 218 may be configured to enable multiple options of fabrication. The illustrated ridges 218 are spaced 5 degrees apart. Finer or coarser pitch may use in different embodiments depending on fabrication specifications. Also, the ridges 302 and 218 may be replaced by texture surfaces. The ridged surfaces on the linking element 300 and the rod connection element 200 may be configured to have different diameters such that the linking element 300 and the rod connection element 200 may pivot and rotate relative to each other when not locked as shown in FIG. 9.

In an embodiment, once the linking element 300 is snapped onto the rod connection element 200, the tabs 202 may be broken off by levering each tab 202 with a mating tool (not shown). The interface between the tabs 202 and the upper portion 204 of the rod connection element 200 may be configured to include internal and external grooves 220 to improve the ease of breaking off the tabs 202. After the tabs 202 are broken off, a fastener 400 may be tighten to clamp the rod 212. As the fastener 400 is tightened, the upper portion 204 and the ridges 218 are forced outward due to a lateral compression force exerted by the fastener 400. As such, the outward movement of the ridges 218 allows them to engage the ridges 302 of the linking element 300, thereby substantially fixing the rod connection element 200 in a rotational orientation relative to the longitudinal axis 402.

Figure 11:
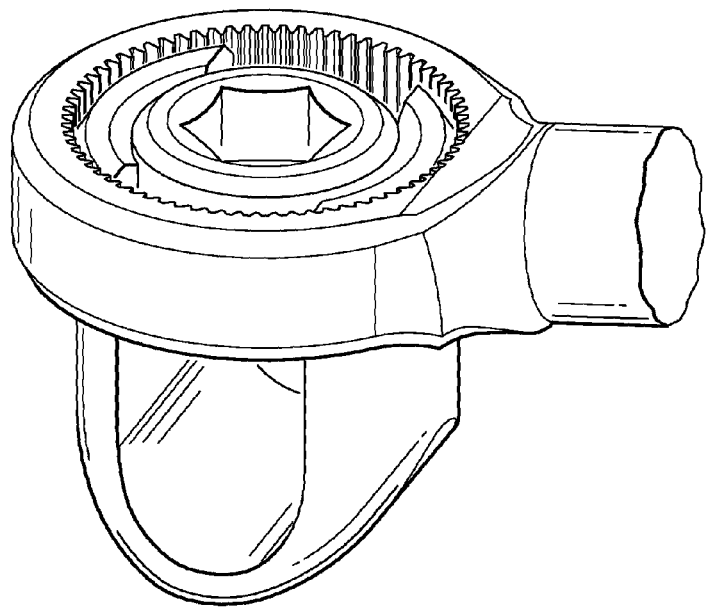
FIG. 11 illustrates a perspective view of an exemplary linking element rotationally fixed with respect to an exemplary rod connection element without a rod disposed therein.

It is to be appreciated that the rod 212 may be disposed in the slot 210 either before or after the linking element 300 and the rod connection element 200 are snapped together. FIG. 11 shows an exemplary embodiment in which the linking element 300 and the rod connection element 200 are fixed as discussed above, and at this stage, the rod 212 can only be inserted laterally.

Figure 12:
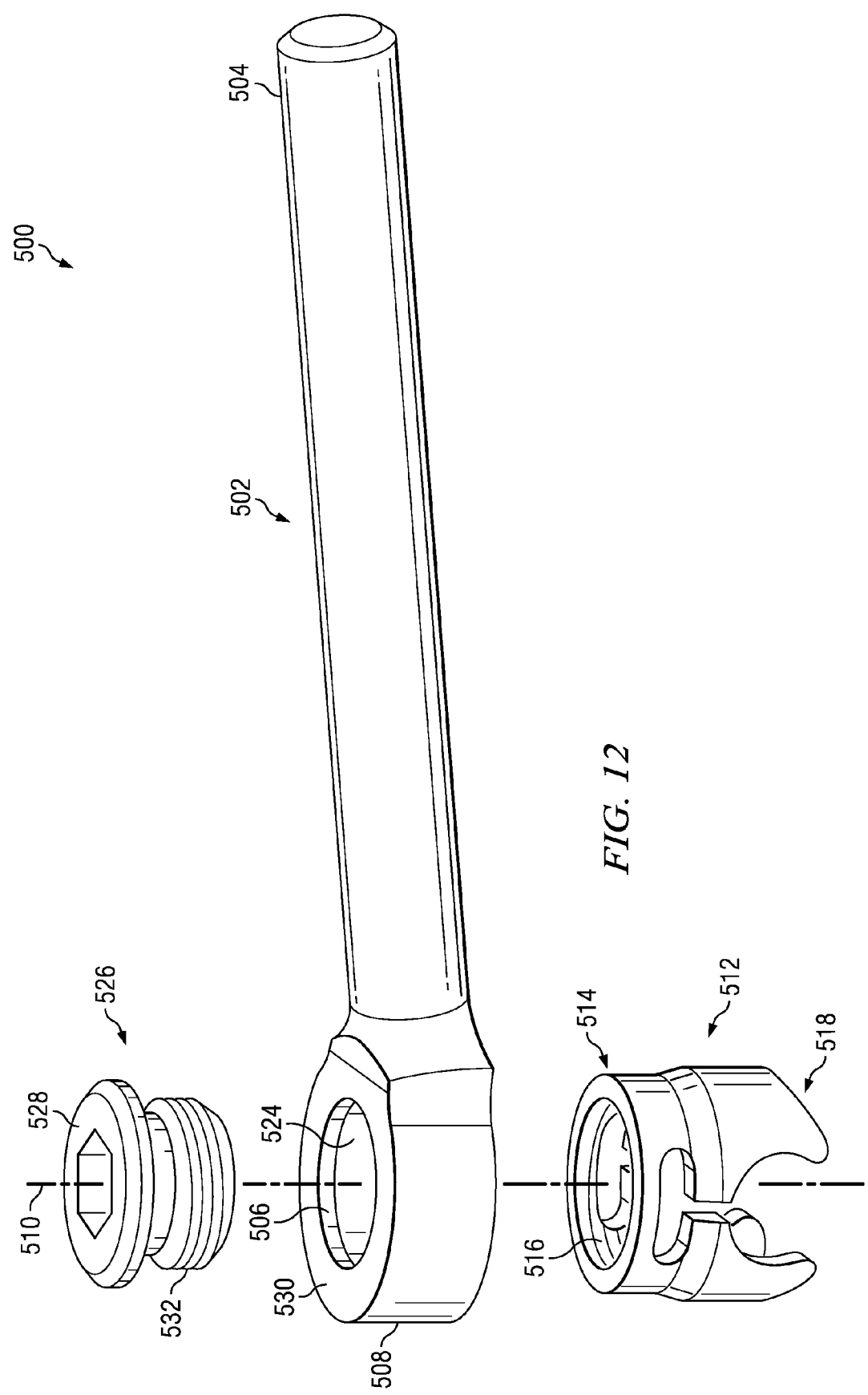
FIG. 12 illustrates an explode view of another exemplary embodiment of a connector system.

FIG. 12 and FIG. 13 illustrate an exemplary embodiment of an orthopedic connector system 500 before and after assembly, respectively. FIG. 14 is a cross-sectional view of the orthopedic connector system 500 in an assembled state. Referring to FIGS. 12-14, an exemplary embodiment of the orthopedic connector system 500 may include a linking element 502 having an end portion 504 operable to be connected to a fastening device (not shown), such a pedicle screw. The linking element 502 may also include an aperture 506 defined in an offset portion 508 of the linking element 502 offset from the end portion 504 The aperture 506 may extend along a first longitudinal axis 510. The end portion 504 of the linking element 502 may have a variety of configurations, including a rod-like geometry as shown in FIGS. 12-14. The aperture 506 may be offset from the end portion 504 by various distances and angles, depending on the surgical applications and the anatomical constraints in each application.

The orthopedic connector system 500 may also include a rod connection element 512 having an upper portion 514 operable to be received in the aperture 506 and a tapered flexible lower portion 518 operable to clamp onto a construct rod. An embodiment of the rod connection element 512 includes an opening 516 defined in the upper portion 514 of the rod connection element 512, and the opening 516 may be configured to extend longitudinally along and circumferentially about the first longitudinal axis 510 as illustrated in FIGS. 12-14. The linking element 502 is operable to rotate about the first longitudinal axis 510 relative to the rod connection element 512.

The orthopedic connector system 500 may also include a fastener 526 having a head portion 528 operable to latch against a top surface 530 of the offset portion 518. The fastener 526 may also have a body portion 532 operable to be received in the 516 opening of the rod connection element 512. In an embodiment, a rotation of the fastener 526 may be operable to effect: a) a translation of the rod connection element 512 upwardly towards the top surface 530 of the offset portion 508; and b) a compression of the tapered flexible lower portion 518 of the rod connection element against an inner wall 524 of the offset portion 508 of the linking element 502. The compression of the tapered flexible lower portion 518 may be operable to substantially fix the linking element 502 in a rotational orientation relative to the rod connection element 512 about the first longitudinal axis 510 and substantially fix the rod in a longitudinal position relative to the rod connection element 512.

In operation, a construct rod (not shown) may be already implanted in a surgical site, and the rod connection element 512 is snapped onto the construct rod (not shown). The upper portion 514 of the rod connection element 512 may be received in the aperture 506 of the linking element 502, and the end portion 504 of the linking element 502 is passed thru a pedicle screw slot (not shown). A set screw (not shown) may be provisionally added to the pedicle screw to keep the linking element 502 in place while still enabling some movement. The fastener 526 may be provisionally tightened to secure the rod in the rod connection element 512. As the fastener 526 is tightened, the rod connection element 512 is drawn up into the aperture 506, where the tapered flexible lower portion 518 of the rod connection element 512 is compressed by the aperture 506's chamfered surface. This action initiates rod clamping while simultaneously clamping the relative rotational position of the linking element 502 to the rod connection element 512. The pedicle screw set screw may then be tightened to secure the linking element 502 to the pedicle screw.

It is to be appreciated that while the connector system 500 is constructed differently from the connector system 100, the above discussed benefits allowed by the configuration of the connector system 100, including an additional degree of rotation and ease of attachment, may be realized by the connector system 500.

While various embodiments in accordance with the principles disclosed herein have been described above, it should be understood that they have been presented by way of example only, and not limitation. Thus, the breadth and scope of this disclosure should not be limited by any of the above-described exemplary embodiments, but should be defined only in accordance with any claims and their equivalents issuing from this disclosure. Furthermore, the above advantages and features are provided in described embodiments, but shall not limit the application of such issued claims to processes and structures accomplishing any or all of the above advantages.

Additionally, the section headings herein are provided for consistency with the suggestions under 37 CFR 1.77 or otherwise to provide organizational cues. These headings shall not limit or characterize the embodiment(s) set out in any claims that may issue from this disclosure. Specifically and by way of example, although the headings refer to a "Technical Field," the claims should not be limited by the language chosen under this heading to describe the so-called field. Further, a description of a technology in the "Background" is not to be construed as an admission that certain technology is prior art to any embodiment(s) in this disclosure. Neither is the "Summary" to be considered as a characterization of the embodiment(s) set forth in issued claims. Furthermore, any reference in this disclosure to "invention" in the singular should not be used to argue that there is only a single point of novelty in this disclosure. Multiple embodiments may be set forth according to the limitations of the multiple claims issuing from this disclosure, and such claims accordingly define the embodiment(s), and their equivalents, that are protected thereby. In all instances, the scope of such claims shall be considered on their own merits in light of this disclosure, but should not be constrained by the headings set forth herein.

What is claimed is:

1. An orthopedic connector system comprising:
   a linking element having:
      a rod-like cylindrical end portion operable to be securable within a pedicle screw; and
      an aperture defined in a flat lower surface in an offset portion of the linking element offset from the end portion, the aperture extending along a first longitudinal axis;
   a rod connection element having a solid lower portion and an upper portion operable to be received in the aperture, wherein the linking element is operable to rotate about the first longitudinal axis relative to the rod connection element and comprises:
      an opening defined in the upper portion of the rod connection element, the opening extending longitudinally along and circumferentially about the first longitudinal axis; and
      an elongated slot defined in the solid lower portion of the rod connection element, the elongated slot operable to seat a rod therein;
      wherein the rod is operable to be received within the rod connection element from the opening in the upper portion to the elongated slot in the lower portion; and
   a fastener operable to be received in the aperture of the linking element and the opening of the rod connection element, wherein
      the fastener is operable to actuate a connection mechanism to substantially fix the linking element in a rotational orientation relative to the rod connection element about the first longitudinal axis and substantially fix the rod in a longitudinal position relative to the rod connection element.

2. The connector system of claim 1, wherein the connection mechanism comprises:
   a first compression force exerted by the fastener on the upper portion of the rod connection element against an inner wall of the offset portion to substantially fix the linking element in a rotational orientation relative to the rod connection element about the first longitudinal axis; and
   a second compression force exerted by the fastener on the rod against the elongated slot to substantially fix the rod in a longitudinal position relative to the elongated slot.

3. The connector system of claim 2, wherein the upper portion of the rod connection mechanism and the offset portion of the linking element comprise mating ridges defined therein, and the first compression force is operable to allow the mating ridges to engage each other.

4. The connector system of claim 1, wherein the offset portion of the linking element comprises a ring disposed in a groove defined in an inner wall of the offset portion of the linking element, and the ring is operable to snap into a mating groove defined in the upper portion of the rod connection element.

5. The connector system of claim 4, wherein the groove in the inner wall has a larger diameter than a diameter of the ring such that the ring is operable to expand into the groove in the inner wall as the linking element is placed over the rod connection element.

6. The connector system of claim 1, wherein the upper portion of the rod connection element comprises outer recessed areas defined therein and extending circumferentially, the outer recessed areas operable to mate with an inner wall of the offset portion of the linking element.

7. The connector system of claim 1, wherein the elongated slot is configured to have an undercut geometry that mates with a geometric profile of the rod.

8. The connector system of claim 7, wherein the rod connection element comprises a latch proximate to the elongated slot.

9. The connector system of claim 1, wherein the fastener comprises a set screw.

10. The connector system of claim 1, wherein the rod connection element comprises tapering tabs extending upwardly from the upper portion of the rod connection element.

11. The connector system of claim 10, wherein the tabs are operable to guide the linking element down to the upper portion of the rod connection element for engagement.

12. The connector system of claim 10, wherein the tabs are operable to be broken off.

13. An orthopedic connector system comprising:
   a linking element having:
      a rod-like cylindrical end portion operable to be securable within a pedicle screw; and
      an aperture defined in an offset portion of the linking element offset from the end portion, the offset defined by a flat lower surface, a flat upper surface, and an inner wall enclosing the aperture, the aperture extending along a first longitudinal axis;
   a rod connection element having an upper portion operable to be received in the aperture defined by the inner wall, wherein the linking element is operable to rotate about the first longitudinal axis relative to the rod connection element and comprises:
      an opening defined in the upper portion of the rod connection element, the opening extending longitudinally along and circumferentially about the first longitudinal axis; and
      a tapered flexible lower portion operable to clamp onto a rod;
   a fastener operable to be received in the opening of the rod connection element, wherein a rotation of the fastener is operable to effect a translation of the rod connection element upwardly towards the upper surface of the offset portion and a compression of the tapered flexible lower portion of the rod connection element against the inner wall of the offset portion of the linking element, the compression operable to substantially fix the linking element in a rotational orientation relative to the rod connection element about the first longitudinal axis and substantially fix the rod in a longitudinal position relative to the rod connection element;

wherein the rod connection element is operable to engage the rod via the tapered flexible lower portion before being received in the inner wall enclosing the aperture via the upper portion.

14. The orthopedic connector system of claim 13, wherein the fastener comprises a head portion operable to latch against the upper surface of the offset portion and a body portion operable to be received in the opening of the rod connection element.

15. A method of assembling a connector system for connecting a medical fastener to a rod in an offset orientation, comprising:
    connecting a rod connection element to an implanted construct rod, wherein the rod connection element is rotatable about an axis formed by the implanted construct rod after engaging the implanted construct rod;
    providing a linking element having:
        a rod-like cylindrical end portion operable to be securable within a pedicle screw; and
        an aperture defined in an offset portion of the linking element offset from the end portion, the offset defined by a flat lower surface, a flat upper surface, and an inner wall enclosing the aperture, the aperture extending along a first longitudinal axis;
    connecting the linking element the rod connection element, and the implanted construct rod such that an upper portion of the rod connection element is disposed in the aperture, wherein the linking element is circumferentially rotatable about the first longitudinal axis after the connecting;
    positioning the linking element in a rotational orientation about the first longitudinal axis relative to the rod connection element;
    disposing a fastener in the aperture of the linking element and an opening defined in the upper portion of the rod connection element, the opening extending longitudinally along and circumferentially about the first longitudinal axis; and
    rotating the fastener to substantially fix the rotational orientation of the linking element relative to the rod connection element and substantially fix the rod in a longitudinal position relative to the rod connection element.

16. The method of claim 15, wherein rotating the fastener causes:
    a first compression force exerted by the fastener on the upper portion of the rod connection element against the inner wall of the offset portion to substantially fix the rotational orientation of the linking element relative to the rod connection element about the first longitudinal axis; and
    a second compression force exerted by the fastener on the rod against an elongated slot of the rod connection element to substantially fix the rod in a longitudinal position relative to the elongated slot.

17. The method of claim 15, wherein the rod connection element comprises a tapered flexible lower portion operable to clamp onto a rod, and the fastener comprising:
    a head portion operable to latch against the upper surface of the offset portion; and
    a body portion operable to be received in the opening of the rod connection element; and
    wherein rotating the fastener causes a translation of the rod connection element upwardly towards the upper surface of the offset portion and a compression of the tapered flexible lower portion of the rod connection element against the inner wall of the offset portion, the compression operable to substantially fix the rotational orientation of the linking element relative to the rod connection element and substantially fix the rod in a longitudinal position relative to the rod connection element.

18. The method of claim 15, wherein disposing the upper portion of the rod connection element in the aperture is performed before connecting the rod to the rod connection element.

19. The method of claim 15, wherein disposing the upper portion of the rod connection element in the aperture is performed after connecting the rod to the rod connection element.

20. The method of claim 15, wherein the fastener comprises a set screw.

* * * * *